United States Patent [19]

Valentine et al.

[11] Patent Number: 5,382,297
[45] Date of Patent: Jan. 17, 1995

[54] ENDOSCOPE CLEANING AND DEFOGGING APPARATUS

[75] Inventors: Douglas E. Valentine, Oakdale; Ronald J. Cerone, East Lyme, both of Conn.

[73] Assignee: Merocel Corporation, Mystic, Conn.

[21] Appl. No.: 126,642

[22] Filed: Sep. 27, 1993

Related U.S. Application Data

[62] Division of Ser. No. 851,536, Mar. 13, 1992, Pat. No. 5,274,874.

[51] Int. Cl.[6] ............................................. A47L 25/00
[52] U.S. Cl. .................................. 134/15; 15/244.1; 15/210.1; 134/42
[58] Field of Search ............... 15/244.1, 244.4, 210.1, 15/214, 104.04, 104.02, 104.03; 134/15, 42

[56] References Cited

U.S. PATENT DOCUMENTS

| | | | |
|---|---|---|---|
| 1,735,046 | 11/1929 | Harris | 118/270 |
| 2,229,071 | 1/1941 | Godstrey | 15/256.6 |
| 2,923,020 | 2/1960 | Fluster | 15/244.1 |
| 3,063,083 | 11/1962 | Obitts | 15/214 X |
| 3,150,406 | 9/1964 | Obitts | 15/214 X |
| 3,413,229 | 11/1968 | Bianco et al. | 252/90 |
| 3,583,016 | 6/1971 | McConnell | 15/244.1 |
| 4,011,617 | 3/1977 | Toelke et al. | 15/104.04 |
| 4,098,728 | 7/1978 | Rosenblatt | 521/141 |
| 4,237,641 | 12/1980 | Gupton | 43/25 |
| 4,282,891 | 8/1981 | Duceppe | 132/73.5 |
| 4,501,220 | 2/1985 | Biasini et al. | 15/104.04 |
| 4,504,994 | 3/1985 | Johnston | 15/214 |
| 4,517,702 | 5/1985 | Jackson | 15/114 |
| 4,533,399 | 8/1985 | Mencke | 134/6 |
| 4,559,662 | 12/1985 | Kunold, Jr. | 15/214 |
| 4,658,894 | 4/1987 | Craig | 15/104.04 |
| 4,716,615 | 1/1988 | Whitehead et al. | 15/244.1 |
| 4,752,983 | 6/1988 | Grieshaber | 15/220.4 |
| 4,779,300 | 10/1988 | Pompe | 15/104.9 |
| 5,016,401 | 5/1991 | Mangus | 51/328 |
| 5,018,237 | 5/1991 | Valley | 15/244.1 |

FOREIGN PATENT DOCUMENTS

W905771 5/1990 WIPO.

OTHER PUBLICATIONS

Advertisement "Auto Suture Laparoscopic System . . . Setting Standards in Safety", Journal of Paparoendoscopic Surgery, vol. 1, No. 2, 1991.
Advertisement, "Dr. Fog", O.R. Concepts, Inc. Roanoke, Tex. 76262, 1990.
Advertisement, "Fred", Dexide, Inc. October 1991.

Primary Examiner—Frankie L. Stinson
Attorney, Agent, or Firm—Ostrolenk, Faber, Gerb & Soffen

[57] ABSTRACT

A device for cleaning and defogging an endoscope. A sponge is impregnated with a composition of water, a glycol and a water soluble wetting agent. The impregnated sponge is packaged in a container designed to facilitate cleaning and defogging of the endoscope. In one embodiment, the impregnated sponge is provided in an open container, and the endoscope is wiped against the impregnated sponge. In another embodiment, the impregnated sponge is provided in a tubular container, into which the endoscope is inserted. In yet another embodiment, the impregnated sponge is provided in a device designed to be attached onto an endoscopic trocar cannula. In yet another embodiment, the impregnated sponge is attached to the surface of a flapper valve in an endoscopic trocar cannula, such that the sponge in contacted by the endoscope when the endoscope is inserted in the cannula.

16 Claims, 3 Drawing Sheets

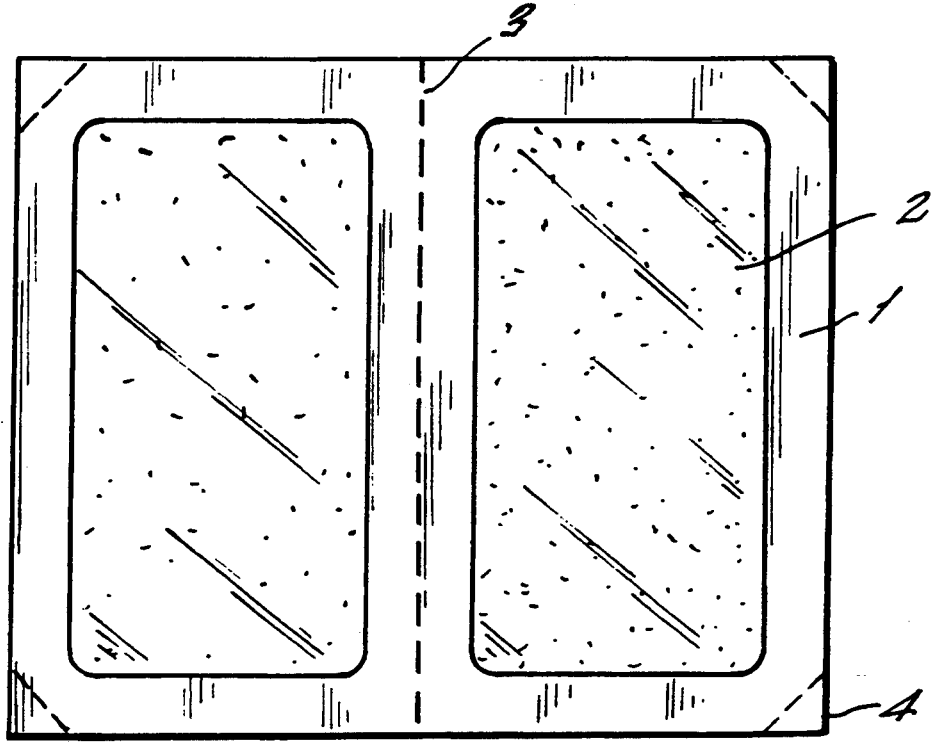
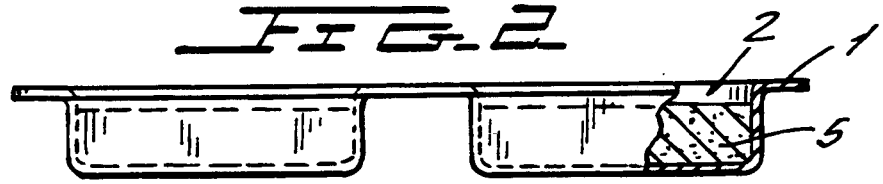
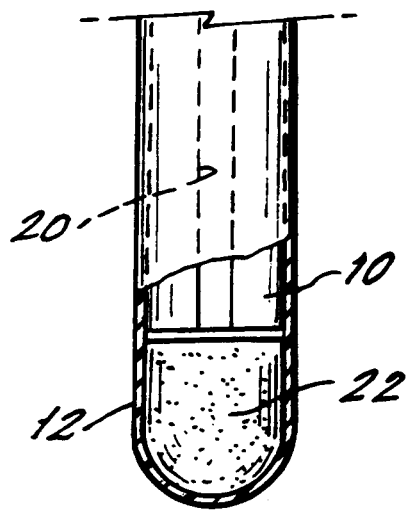
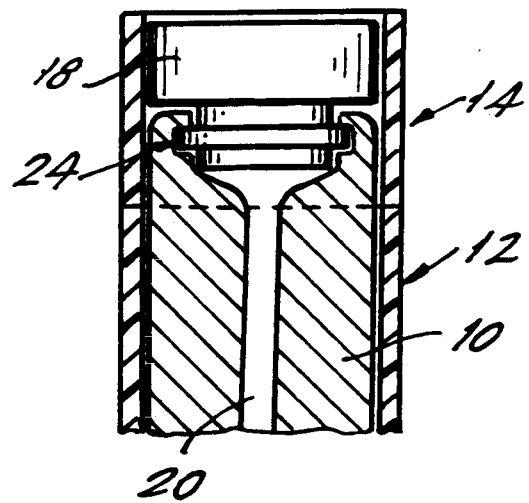

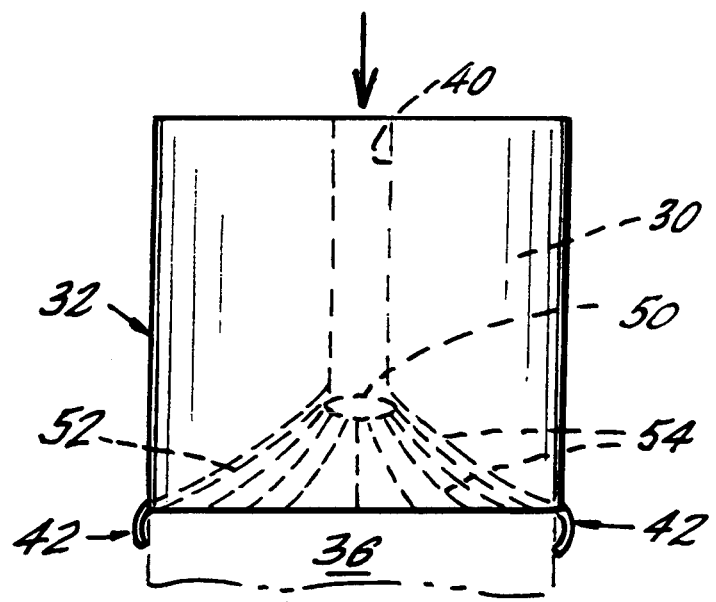
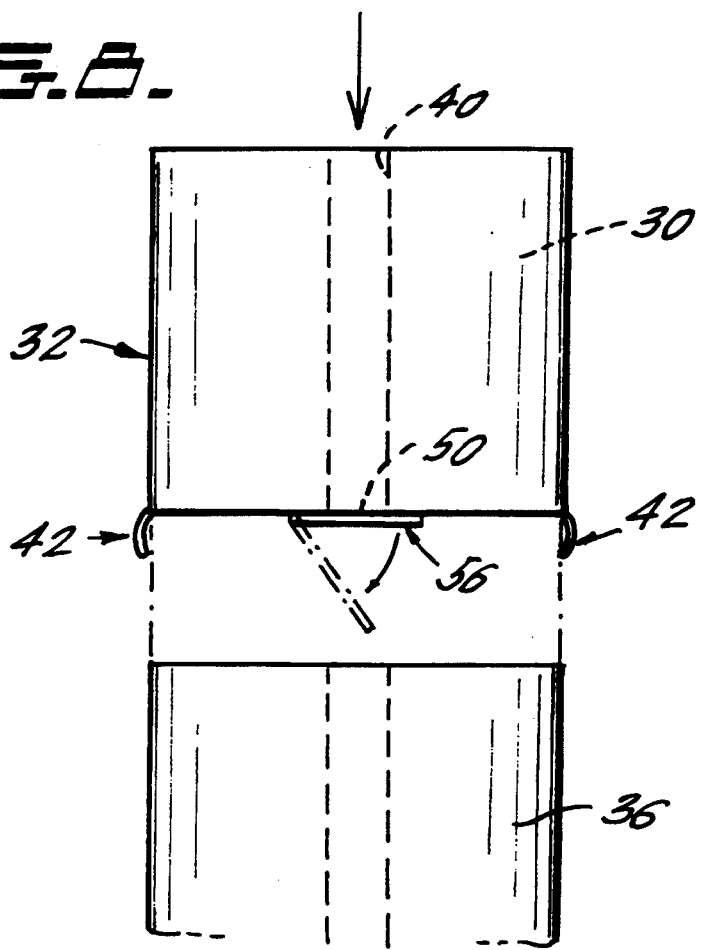

ENDOSCOPE CLEANING AND DEFOGGING APPARATUS

This is a division of application Ser. No. 07/851,536, filed Mar. 13, 1992, now U.S. Pat. No. 5,274,874.

BACKGROUND OF THE INVENTION

1. Field of the Invention

The present invention relates to an apparatus for cleaning and defogging medical instruments and, more specifically, to an impregnated sponge for cleaning and defogging an endoscope.

2. Description of the Related Prior Art

Medical instruments such as surgical endoscopes require regular and careful cleaning. The shaft of an endoscope must be cleaned of bodily residues accumulated during use. A soiled endoscope lens must not only be cleaned, but also defogged. The cleaning and defogging techniques employed must be effective, and at the same time preserve the efficacy and safety of the endoscope.

One presently available technique for cleaning and defogging surgical endoscopes involves impregnating a sponge with a defogger from a dropper, and then wiping the endoscope with the impregnated sponge. In order to avoid scratching the endoscope lens and/or contaminating the endoscope, the sponge should be lint-free and free of foreign materials. Moreover, the sponge should have high water absorption to promote faster wicking of the solution within the sponge and to provide effective cleaning and defogging action at the point of contact with the endoscope. This unique combination of features is not present in the sponges which are currently used for cleaning and defogging endoscopes.

Additionally, the sponges currently in use must be periodically saturated with the defogger. Moreover, none of the endoscope defogging systems presently available offer the convenience of cleaning the endoscope shaft simultaneously with cleaning and defogging the endoscope lens. Finally, none of the available products provide a method of cleaning and defogging an endoscope as it is inserted or removed from an endoscopic trocar cannula.

U.S. Pat. No 4,517,702 to Jackson discloses a sponge for cleaning surgical endoscopes including an axial central bore sized to fit the endoscopic shaft and a slit extending the length of the bore to permit the sponge to fit on the shaft. In Jackson, the endoscope shaft is cleaned by the rubbing action of the sponge against the endoscope. A separate brush attachment is used to clean the lens. However, Jackson, and other products presently available, do not provide an effective, inexpensive apparatus utilizing a sponge with the important features discussed above.

Hence, there is a need for such an effective and safe apparatus for cleaning and defogging surgical endoscopes.

SUMMARY OF THE INVENTION

The present invention provides a lightweight, efficient and inexpensive apparatus for cleaning and defogging medical instruments, particularly endoscopes. In one embodiment, the present invention is provided in the form of a biocompatible, polymeric, elastomeric, lint-free, uniformly swellable hydrophilic sponge impregnated with a defogging and cleaning composition. Such a sponge is disclosed in U.S. Pat. No. 4,098,728 to Rosenblatt, the disclosure of which is hereby incorporated by reference.

The aforementioned sponge, hereinafter referred to as the Rosenblatt sponge, is impregnated with a defogging and cleaning composition including water, a glycol, and a water soluble wetting agent. Preferably, the defogging and cleaning composition includes glycerol and a polyoxyethylene/propylene block polymer as active ingredients.

In another embodiment, the present invention is provided in the form of a kit consisting of a sponge impregnated with a defogging and cleaning composition packaged in a suitable container. Preferably, the sponge is the Rosenblatt sponge impregnated with a defogging and cleaning composition of water, a glycol, and a water soluble wetting agent. Glycerol and a polyoxyethylene/propylene block polymer are preferred active ingredients in the defogging and cleaning composition.

The impregnated sponge may be packaged in a small well having one side open such that cleaning and defogging is accomplished by wiping the lens across a surface of the sponge. Alternatively, the defogging and cleaning kit may consist of two side-by-side wells; one containing a sponge impregnated with the cleaning and defogging composition and the other containing a sponge pre-moistened with a cleaning solution such as a saline solution. In this case, cleaning and defogging is accomplished by first rubbing the instrument lens across the sponge impregnated with the cleaning and defogging composition and then across the sponge with the cleaning solution.

In a further embodiment, the present invention may be provided in the form of a sponge impregnated with a cleaning and defogging composition packaged in a tubular container; the container may be rigid or flexible. Preferably, the sponge is the Rosenblatt sponge and the cleaning and defogging composition includes water, a glycol, and a water soluble wetting agent; glycerol and a polyoxyethylene/propylene block polymer are preferred active ingredients for the cleaning and defogging composition. The container is provided with a cap to prevent drying of the pre-moistened sponge. A guide is preferably provided in the mouth of the tube to facilitate insertion of the instrument into the sponge. The guide in the mouth of the tube can be funnel shaped, and include an arrangement for securing the impregnated sponge in place in the tubular container. Additionally, the impregnated sponge may be provided in two separate sections, and with an arrangement optionally provided for securing the two sections together. Alternatively, the impregnated sponge (in one or two sections) can be attached to the tubular container with an adhesive.

In the tubular embodiment, an elongated instrument (preferably a surgical endoscope) is inserted in the container, past the guide fit in the mouth of the container, and into the impregnated sponge. The instrument is rubbed against the sponge to clean the portion of the shaft inserted in the sponge and also simultaneously to clean and defog the instrument lens. After cleaning, the instrument is withdrawn from the container.

In yet another embodiment, the present invention is provided in the form of a sponge impregnated with a cleaning and defogging composition placed in a suitable container which can be attached to an endoscopic trocar cannula. Preferably, the sponge is the Rosenblatt sponge, and the cleaning and defogging composition includes water, a glycol, and a water soluble wetting agent; glycerol and a polyoxyethylene/propylene block polymer are the preferred active ingredients for the cleaning and defogging composition. The container is provided with a guide at the opening leading into the sponge to facilitate insertion of the instrument through an axially aligned aperture in the sponge to a second opening in the container leading to the trocar cannula. The container is attachable to the trocar cannula.

The guide at the opening is preferably funnel-shaped. Additionally, an arrangement for entrapping the cleaning and defogging composition in the sponge can be provided at the second opening to the container leading to the cannula; the entrapment arrangement can take the form of an elevated floor in the area of the second opening having the shape of an inverted funnel. Alternatively, passage of the defog solution into the cannula can be prevented by providing a gasket, a spring loaded valve, a toilet seat valve or an iris valve at the second opening. Moreover, as before, the impregnated sponge can be provided in two portions, with one portion attached to the aforementioned valve or gasket.

In yet another embodiment, a sponge, such as the Rosenblatt sponge, impregnated with a cleaning and defogging compositions is placed directly in an endoscopic trocar cannula, preferably on the outer face of the valve inside the trocar cannula.

Cleaning and defogging of the surgical endoscope, or other medical instruments used with a trocar cannula, is accomplished by rubbing the portion of the instrument inserted in the container against the impregnated sponge. In this manner, the shaft of the instrument is cleaned and, simultaneously, the instrument lens is cleaned and defogged. Alternatively, during use in the trocar cannula, the instrument may be withdrawn into the container having the impregnated sponge, rubbed against the sponge to clean and defog the instrument, and then returned back into the trocar cannula.

In all embodiments of the invention, the sponge may include an abrasive.

Other features and advantages of the present invention will become apparent when the following description of the invention is read in conjunction with the accompanying drawings.

BRIEF DESCRIPTION OF THE DRAWING(S)

FIG. 1 is a perspective top view of the invention in the form of an impregnated sponge packaged in a small well;

FIG. 2 is a side view of FIG. 1;

FIG. 4 is a partial, cross-sectional view taken along lines A—A of FIG. 1 showing the impregnated sponge.

FIG. 5 is a partial, cross-sectional view taken along lines B—B of FIG. 1 showing an arrangement for securing the impregnated sponge.

FIGS. 7 and 8 are side views of the device of FIG. 6, showing alternative entrapment arrangements for preventing the cleaning and defogging solution from entering the cannula.

DETAILED DESCRIPTION OF THE PREFERRED EMBODIMENTS

Figure 3:
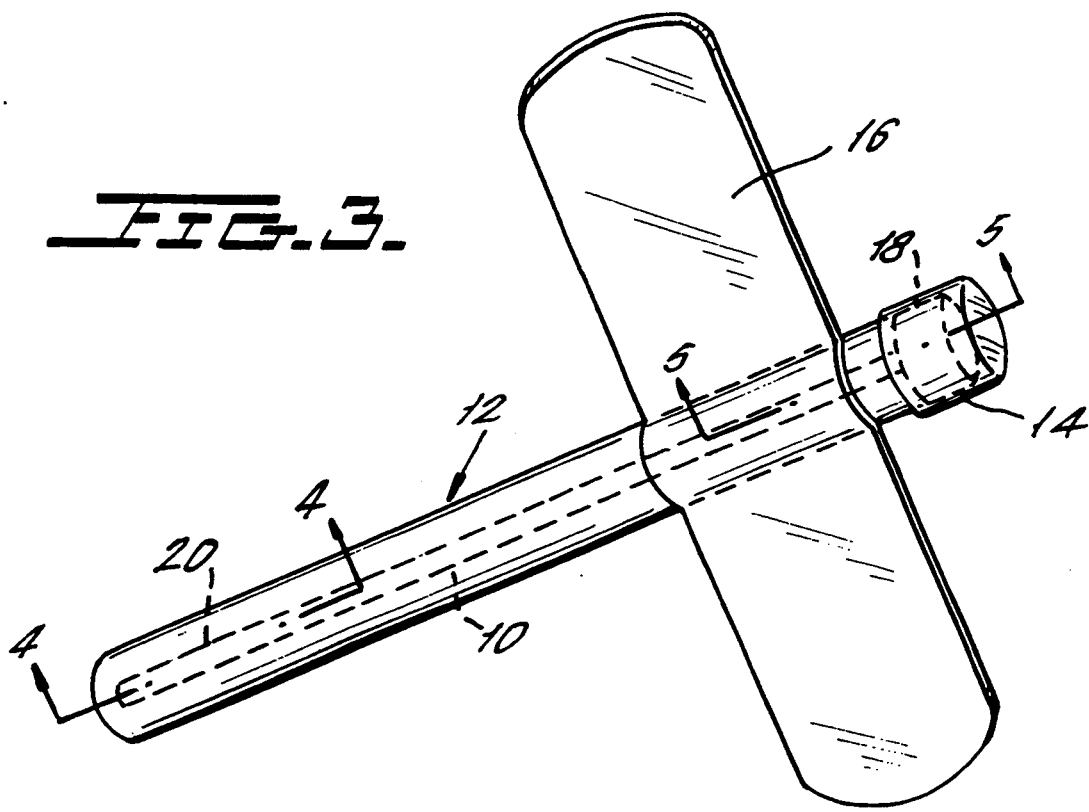
FIG. 3 is a perspective view of the invention in the form of a tubular container housing an impregnated sponge.

In its basic form, the present invention consists of a high absorption, lint-free, fiber free sponge impregnated with a cleaning and defogging composition. The sponge may be suitably packaged as a pre-moistened wipe. This unique combination provides cleaning and defogging of a soiled endoscope lens when it is wiped across the sponge pad. Furthermore, the impregnated sponge can be packaged in a small well. Alternatively, cleaning and defogging can be accomplished in discrete steps with sponges in two different wells. Moreover, the endoscopic shaft can be cleaned of bodily residues simultaneously with the cleaning and defogging of the lens by incorporating the pre-moistened sponge in a tubular package. In each case, the sponge pad is ready for use immediately after opening the package.

Preferably, the Rosenblatt sponge is used in the present invention, although any sponge having comparable characteristics can be used. Barium sulfate, silica, alumina, and other abrasives known in the art may be added during the sponge polymerization process to impart an abrasive quality to the sponge. Control of the abrasive content allows optimization of the cleaning of the residues from the entire medical instrument, or from selected portions such as the lens or shaft.

The density of the sponge material can be controlled to produce a soft, non-scratching surface for contact with the endoscopic lens during cleaning and defogging. The density of the sponge is preferably in the range of 0.8–1.2 grams/cc.

The cleaning and defogging composition impregnated in the sponge includes water, a glycol, and a water soluble wetting agent. Preferably, glycerol and a polyoxyethylene/propylene block polymer are the active ingredients used in the cleaning and defogging composition. The glycerol content may vary from 5–20%, preferably from 8–12%, by volume. A polyoxyethylene/propylene block polymer or an equivalent water soluble wetting agent in an aqueous solution having a concentration of 10–50%, preferably 25–40%, is prepared separately and then added to the water/glycol mixture at the volumetric concentration of 2–15%, preferably 4–8%. A suitable dye, such as Green Dye, FD&C #5, or an equivalent water soluble dye prepared in a concentration of 6–20 gram/gal., preferably 8—12 grams/gal., and stabilized with 5–28 cc/gal., preferably 12–20 cc/gal., of glacial acetic acid, may be included in the cleaning and defogging composition. A conventional preservative, such as potassium sorbate, sorbic acid, sodium benzoate and benzoic acid, may be added to the composition, preferably in a quantity of about 1/10 of 1% by volume. The solution including the above ingredients is agitated to dissolve all the components and refrigerated before use. The cleaning and defogging solution is preferably added to the sponge during product manufacture.

An example of a suitable cleaning and defogging composition is as follows:

EXAMPLE

A homogeneous aqueous cleaning and defogging composition is prepared by mixing 900 cc. water with 10% by volume glycerol. A 35% concentration aqueous solution of a polyoxyethylene polyoxypropylene block polymer is prepared separately and then added to the water/glycerol mixture at a volumetric concentration of 6%. FD&C #5, green dye, is prepared in a concentration of 10 grams/gal and stabilized with 15 cc/gal of glacial acetic acid. 1/10 of 1% by volume of a preservative is also added to the mixture. The mixture is agitated to dissolve all components and added to the sponge during product manufacture.

Referring now to the drawings, wherein like numbers indicate like elements, FIGS. 1 and 2 show one embodiment of the present invention wherein the pre-moistened sponge of the present invention is blister packaged in a small well 1 having an opening 2 so that one face of the sponge 5 is exposed. In the preferred embodiment, the well 1 has dimensions of 3"×1 9/16" and a depth of 7/16". The lens of the endoscope is cleaned and defogged by wiping it across the surface of the sponge. To avoid any possibility of contamination of the sponge prior to use, the sealed well containing the impregnated sponge 5 can be distributed in a blister pack tray (not shown).

Alternatively, two pre-moistened sponges may be provided in adjacent wells as shown in FIGS. 1 and 2, one impregnated with the cleaning and defogging solution and the other with a cleaning solution such as a saline solution. The endoscope lens is first rubbed on the surface of the sponge with the defogging and cleaning composition and then on the sponge containing only a cleaning solution. The packaging can further include a suitable outer container blister package, as in the single well embodiment.

Moreover, in both embodiments an adhesive strip with a removable protective strip, Velcro ®, or any other suitable attachment vehicle known in the art may be provided for attaching the kit to a support such as a surgical drape or a mayo stand.

FIG. 3 shows an embodiment of the present invention for cleaning and defogging an endoscope in which the impregnated sponge 10 is packaged in a tubular container 12. The kit includes a cap 14 to prevent drying of the pre-moistened sponge 10, an adhesive tape 16 for attaching the kit to a support such as a surgical drape, and a guide 18 to facilitate insertion of the medical instrument into the tube annulus.

The sponge 10 includes an axially aligned central aperture 20 extending substantially along the length of the sponge 10. The aperture 20 is sized to accommodate the lens and shaft of an endoscope. The aperture 20 can be formed in any manner suitable for the practice of the invention. For example, a flat impregnated sponge pad may be curled into a closed C-shape and then placed in the tube; alternatively, for use with thinner endoscopes, a cylindrical shaped sponge can be manufactured with a slit extending substantially along the length; for larger endoscopes, a cylindrical sponge can be provided with a central longitudinal bore.

The sponge 10 can be provided as a single piece, or, as shown in FIG. 4, as two separate sections 10 and 22. In the latter embodiment, the upper section 10 lines the internal periphery of the tubular container 12; the lower section 22 is in the form of a solid plug placed in the bottom of the tubular container 12, thereby preventing the endoscope lens from impact against the bottom of the tubular container 12. In a preferred embodiment, the plug 22 includes abrasive material, whereas the peripheral sponge 10 does not.

The container 12 is preferably constructed from a rigid material such as hard plastic. Alternatively, the container 12 may be a flexible tube. The material of which the container may be constructed include polymeric materials such as thick latex, PVC, or any similar material known in the art. The cap 14 and guide 18 may similarly be constructed of any suitable material known in the art. Additionally, the mouth of the tubular container 12 can be flared into a funnel (shown in FIG. 5), to further facilitate insertion of the endoscope. The guide 18 and the funnel may comprise one piece; alternatively, they can consist of separate components suitably attached to the container 12. The adhesive strip 16 includes a removable protective strip (not shown). The pre-moistened sponge 10 extends along substantially the entire length of the container 12.

The guide 18 is preferably fabricated with a smooth surface from materials such as polypropylene and polyethylene to prevent scratching of the endoscope lens. Guide 18 performs several functions, including: (1) guiding and aligning the endoscope shaft during insertion in the tubular container 12; (2) guiding the tip of the shaft to the central aperture 20; and (3) securing the sponge 10 in place to prevent bunching of the sponge. The securing function is accomplished by a locking arrangement 24 consisting of interlocking parts provided in the guide 18 and the sponge 10 as shown in FIG. 5. As an alternative to the locking arrangement 24, the sponge 10 may be secured with a suitable adhesive. If the sponge is provided in two sections (as described previously), a similar locking arrangement can be provided between the two sections of the sponge to prevent peripheral section 10 from moving upward within the tube when the endoscope is withdrawn.

To clean and defog an endoscope, the endoscope is inserted into the container 12, through the guide 18, and into the aperture 10 of the pre-moistened sponge 10. A back and forth rubbing movement of the inserted portion of the endoscope against the sponge 20 will clean the shaft of the endoscope, and will simultaneously clean and defog the endoscope lens.

Figure 6:
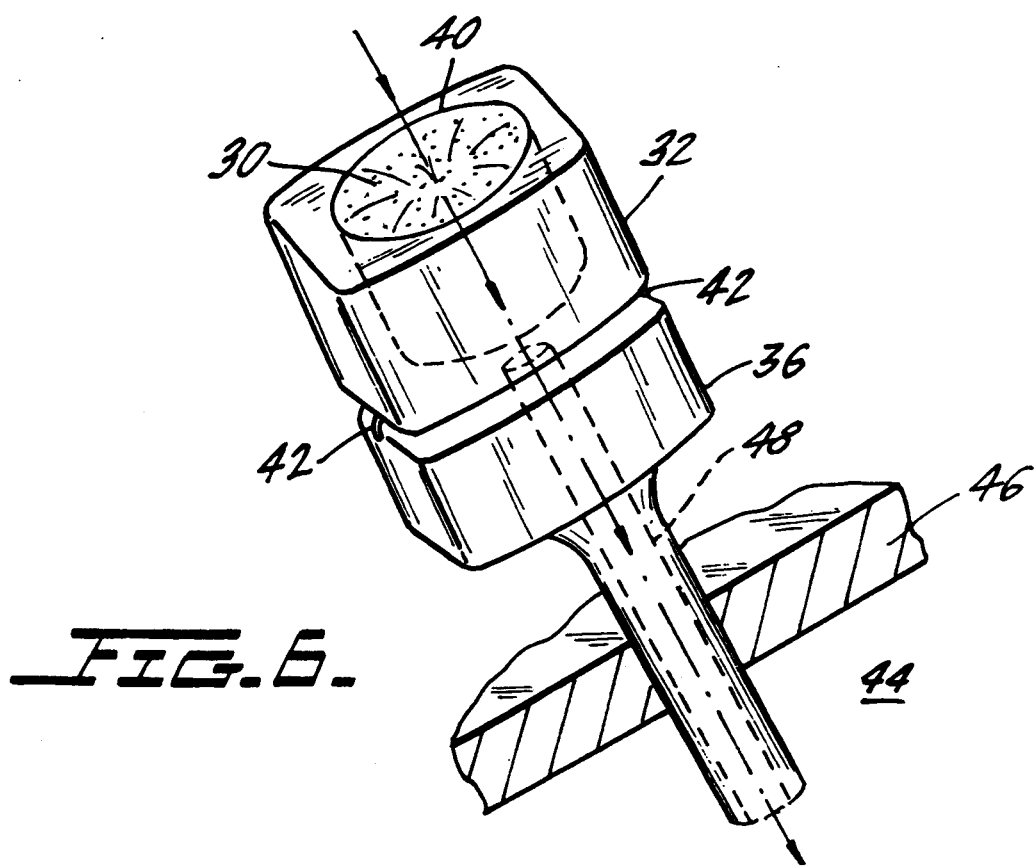
FIG. 6 is a perspective view of the invention in an embodiment which can be attached to an endoscopic trocar cannula inserted into a body cavity through the dermal layers.

FIG. 6 shows an embodiment of the present invention in which an impregnated sponge 30 is packaged in a container 32 which can be attached to an endoscopic trocar cannula 36. The container 32 may be of any shape suitable for use with the trocar cannula 36; additionally, as before, the container 32 may be constructed of hard plastic, or may be made of flexible material and preferably includes a guide (not shown) at the outer opening 40. The pre-moistened sponge 30 is disposed in a central cavity of the container 32. A device 42 is provided for attaching the container 32 to the trocar cannula 36. Device 42 may comprise a clip, an O-ring type attachment, a press-fit type attachment, or any other conventional means for attachment known in the art.

Additionally, the container 32 preferably includes an entrapment arrangement, shown in FIGS. 7 and 8, provided at the inner opening 50 leading to the trocar cannula 36. The entrapment arrangement prevents the cleaning and defogging solution contained in the impregnated sponge 30 from seeping into the trocar cannula 36 and the body cavity 44. One such arrangement, shown in FIG. 7, involves raising the floor 54 of the container 32 at the area of the lower opening so as to create an inverted funnel whereby excess solution will be collected and reabsorbed in sponge 30 at an area 52 around the second opening 50. Alternatively, a valve 56, shown in FIG. 8, can be provided at the opening 50 to prevent the cleaning and defogging composition from entering the cannula 36. Suitable valves for use include a spring loaded flapper valve (shown in FIG. 8), a toilet seat valve and an iris valve. As before, a drip collection and reabsorption area (not shown) can be provided along the internal periphery of the container 32 around the second opening 50. The valve 56 is designed such that it is normally closed, yet is opened by the pressure exerted when the endoscope is pushed through the aperture 40. Additionally, a sponge impregnated with the cleaning and defogging composition can be attached to the inner surface of valve 56 with a suitable adhesive. In yet another variation, a slotted gasket can be used in place of the valve 56. The gasket covers the opening 50, yet allows passage of the endoscope through a slot provided in the gasket material while preventing the cleaning and defogging composition from entering the cannula 36. As before, the surface of the gasket inside the container 32 may be covered with an impregnated sponge.

The trocar cannula in FIG. 6 is shown inserted in a body cavity 44 through the dermal layer 46. One method of cleaning and defogging a surgical endoscope comprises inserting the endoscope through the aperture/guide 40 into the pre-moistened sponge 30. A back and forth rubbing action cleans the shaft of the endoscope and cleans and defogs the lens of the endoscope. After cleaning, the endoscope is pushed into the bore 48 of the trocar cannula 36 for use in the operative cavity 44.

Alternatively, an endoscope in use in a trocar cannula 36 can be pulled back up out of the cannula bore 48 and into the container 32. The portion of the endoscope pulled up into the aperture 40 in the pre-moistened sponge 30 is cleaned and defogged by rubbing it against the sponge 30. After the shaft of the endoscope has been cleaned and the lens has been cleaned and defogged, the endoscope can then be returned into the operative cavity 44.

In yet another embodiment of the present invention, an impregnated sponge can be attached with a suitable adhesive onto the surface of a flapper valve within the trocar cannula, thereby providing cleaning and defogging action when the endoscope is inserted into the trocar cannula, through the valve, and into the body cavity.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An apparatus for cleaning and defogging a medical instrument, comprising:
   a) a sponge impregnated with a defogging and cleaning composition, wherein said sponge has a uniform pore geometry and pore size distribution throughout its volume and comprises the inorganic acid-catalyzed reaction product of formaldehyde and polyvinyl alcohol, said sponge having an initial water absorption and a wicking point of a maximum of 10 seconds of contact with fluid and a variation in the size of the diameter of the pores of less than about 8 to 1 as determined by a stereoscopic microscope eyepiece; and
   b) means for retaining the sponge at the entrance to an endoscopic trocar cannula.

2. The apparatus of claim 1, wherein said defogging and cleaning composition comprises:
   a) water;
   b) a glycol; and
   c) a water soluble wetting agent.

3. The apparatus of claim 2, wherein said glycol comprises glycerol.

4. The apparatus of claim 2 wherein said wetting agent is a polyoxyethylene/propylene block polymer.

5. An apparatus for cleaning and defogging a medical instrument, comprising:
   a) a sponge impregnated with a defogging and cleaning composition; and
   b) means for retaining the sponge at the entrance to an endoscopic trocar cannula, wherein said means for retaining the sponge comprises a container provided with:
      i) a first opening;
      ii) means disposed at said first opening for guiding insertion of said medical instrument into said sponge;
      iii) a second opening; and
      iv) means at said second opening for attaching said container to said cannula.

6. The apparatus of claim 5, wherein said means for guiding is a funnel-shaped insert.

7. The apparatus of claim 5, wherein said second opening further comprises means for entrapment of said defogging and cleaning composition.

8. The apparatus of claim 7, wherein said means for entrapment is selected from a group consisting of a raised floor at said second opening in the form of an inverted funnel, a gasket, a spring loaded flapper valve, and an iris valve.

9. The apparatus of claim 8, wherein said sponge comprises two portions, one of which is secured to said means for entrapment.

10. The apparatus of claim 5, wherein said defogging and cleaning composition comprises:
    a) water;
    b) a glycol; and
    c) a water soluble wetting agent.

11. The apparatus of claim 10, wherein said glycol comprises glycerol.

12. The apparatus of claim 10, wherein said wetting agent is a polyoxyethylene/propylene block polymer.

13. An apparatus for cleaning and defogging a medical instrument, comprising a sponge impregnated with a defogging and cleaning composition, said sponge being disposed within an endoscopic trocar cannula, wherein said sponge is attached to a surface of a valve disposed within said cannula, said surface being contacted by said medical instrument when said medical instrument is inserted in said cannula.

14. The apparatus of claim 13, wherein said sponge has a uniform pore geometry and pore size distribution throughout its volume and comprises the inorganic acid-catalyzed reaction product of formaldehyde and polyvinyl alcohol, said sponge having an initial water absorption and a wicking point of a maximum of 10 seconds of contact with fluid and a variation in the size of the diameter of the pores of less than about 8 to 1 as determined by a stereoscopic microscope eyepiece.

15. A method of cleaning and defogging a medical instrument having a shaft and a lens, comprising the steps of:
    a) inserting said instrument into a container attached to an endoscopic trocar cannula such that said instrument contacts a sponge disposed within said container;

b) rubbing said instrument against the sponge to clean said instrument shaft and to clean and defog said instrument lens; and c) passing said instrument through said container into said endoscopic trocar cannula.

16. A method of cleaning and defogging a medical instrument having a shaft and a lens, comprising the steps of:

a) withdrawing said instrument from a endoscopic trocar cannula into a container attached to the entrance to said cannula, such that said instrument contacts a sponge disposed with said container;

b) rubbing said instrument against said sponge to clean said instrument shaft and to clean and defog said instrument lens; and c) passing said instrument back through said container into said cannula.

* * * * *